US00PP20956P3

(12) United States Plant Patent
Skelton

(10) Patent No.: US PP20,956 P3
(45) Date of Patent: Apr. 27, 2010

(54) ***ACTINIDIA CHINENSIS* PLANT NAMED 'Y118'**

(50) Latin Name: *Actinidia chinensis*
Varietal Denomination: Y118

(76) Inventor: Donald Skelton, R D 1, Huntly (NZ)

( * ) Notice: Subject to any disclaimer, the term of this patent is extended or adjusted under 35 U.S.C. 154(b) by 0 days.

(21) Appl. No.: 12/072,481

(22) Filed: Feb. 26, 2008

(65) Prior Publication Data

US 2009/0217429 P1 Aug. 27, 2009

(51) Int. Cl.
*A01H 5/00* (2006.01)

(52) U.S. Cl. ..... Plt./156

(58) Field of Classification Search ..... Plt./156
See application file for complete search history.

*Primary Examiner*—June Hwu

(57) ABSTRACT

A new and distinct *Actinidia chinensis* cultivar named 'Y118' is disclosed, characterized by having distinctive yellow flesh fruit, heavy cropping and a seasonal harvest time of late March. Additionally, the new variety produces fruit with very soft, slight pubescence and with a distinctive blunt stylar end shape and square shoulders. The new variety is suitable for commercial production of kiwi fruit.

3 Drawing Sheets

Figure 1:
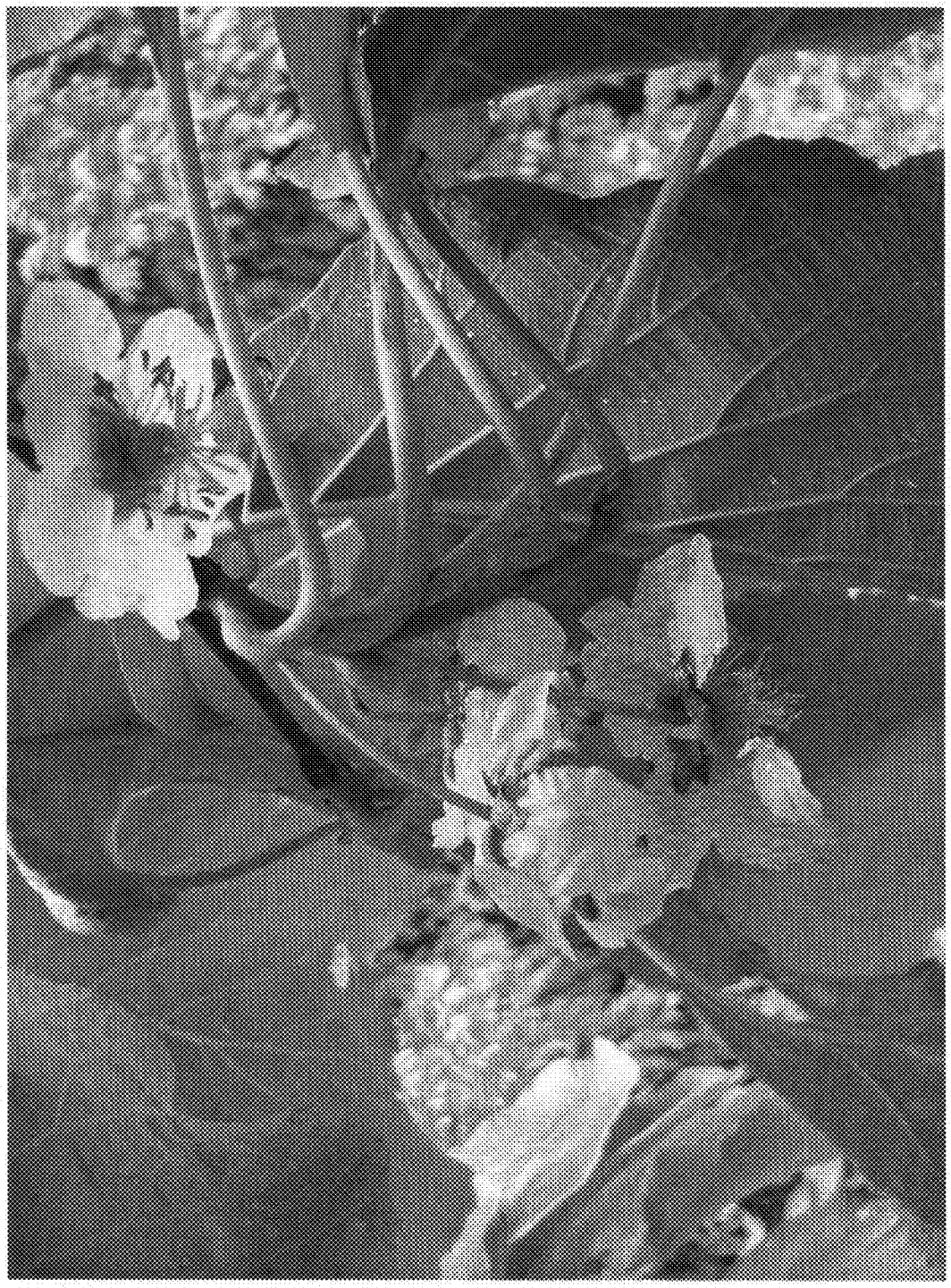

Latin name of the genus and species: *Actinidia chinensis*. Variety denomination: 'Y118'.

BACKGROUND OF THE INVENTION

The new cultivar is a product of a planned breeding program begun in 1975 under the direction of the inventor, Donald Alfred Skelton, a citizen of New Zealand. The seed parent is the unpatented, proprietary seedling variety referred to as *Actinidia chinensis* 'R5' The pollen parent is the unpatented, proprietary seedling variety referred to as *Actinidia chinensis* 'RY.'

Fruit of the new variety was first evaluated in 1999 with favorable results. After the first evaluation, semi-hardwood cuttings were made of 'Y118' and were grafted onto 5 seedling rootstocks 3; of A. *chinensis* and 2 of A. *deliciosa*. Evaluation, asexual propagation and grafting all first took place at the inventor's commercial nursery in Rangiriri, New Zealand in 1999. Subsequent evaluations of the variety have shown the characteristics to be true to type.

SUMMARY OF THE INVENTION

The cultivar 'Y118' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Y118' These characteristics in combination distinguish 'Y118' as a new and distinct *Actinidia chinensis* cultivar:

1. Distinctive yellow flesh fruit
2. Heavy cropping
3. Seasonal harvest time of late March
4. Very soft, downy pubescence that does not adhere strongly to fruit skin.
5. Fruit with a distinctive blunt stylar end shape and square shoulders.

COMPARISON TO PARENT

Plants of the new cultivar 'Y118' are similar to plants of the seed parent, *Actinidia chinensis* 'R5' in most horticultural characteristics, however, plants of the new cultivar 'Y118' produce significantly larger size fruit, with different stylar end characteristics . Additionally, the new variety produces fruit ready to be harvested 8 weeks earlier than 'R5.' Plants of the new cultivar 'Y118' are similar to plants of the male parent, *Actinidia chinensis* 'RY' in most horticultural characteristics, however, plants of the new cultivar 'Y118' produce significantly more female flowers than the male parent.

COMMERCIAL COMPARISON

The new variety is best compared to the commercial variety, 'Hort16A,' U.S. Plant Pat. 11,066. 'Y118' is similar to 'Hort16A' in many horticultural characteristics, however, 'Y118' produces mature fruit approximately 6 weeks earlier than 'Hort16A.' Additionally, the new variety produces an oblong shaped fruit, compared to ovoid. Fruit of the new variety 'Y118' are distinctively blunt, protruding on the stylar end, compared to the strong pointed stylar end shape of 'Hort16A.' Fruit shape differences can also be noted in the shoulder shape. Whereas 'Y118' produces fruit with strongly squared shoulder, 'Hort16A' fruit have rounded shoulders.

BRIEF DESCRIPTION OF THE PHOTOGRAPH

Figure 2:
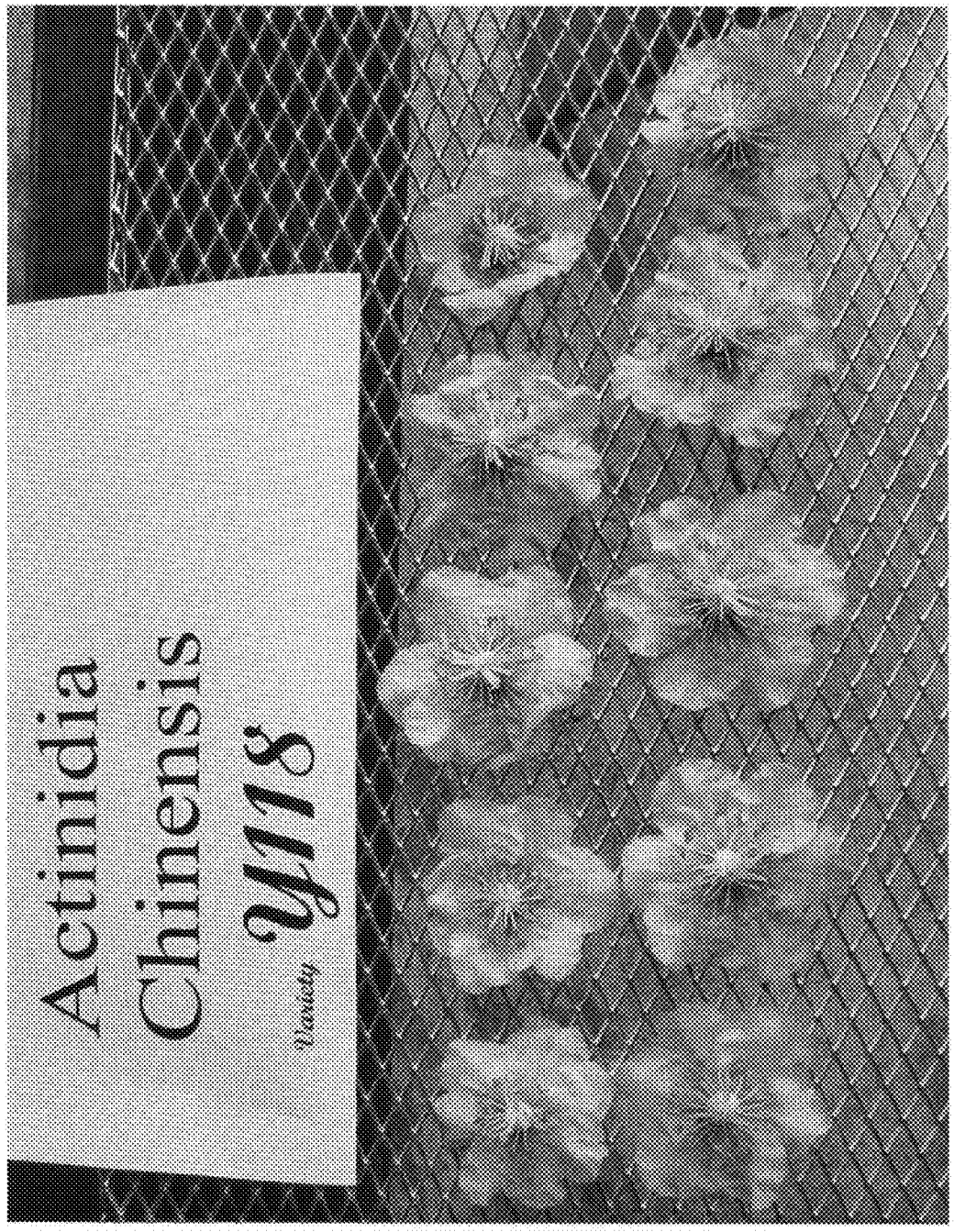
Figure 3:
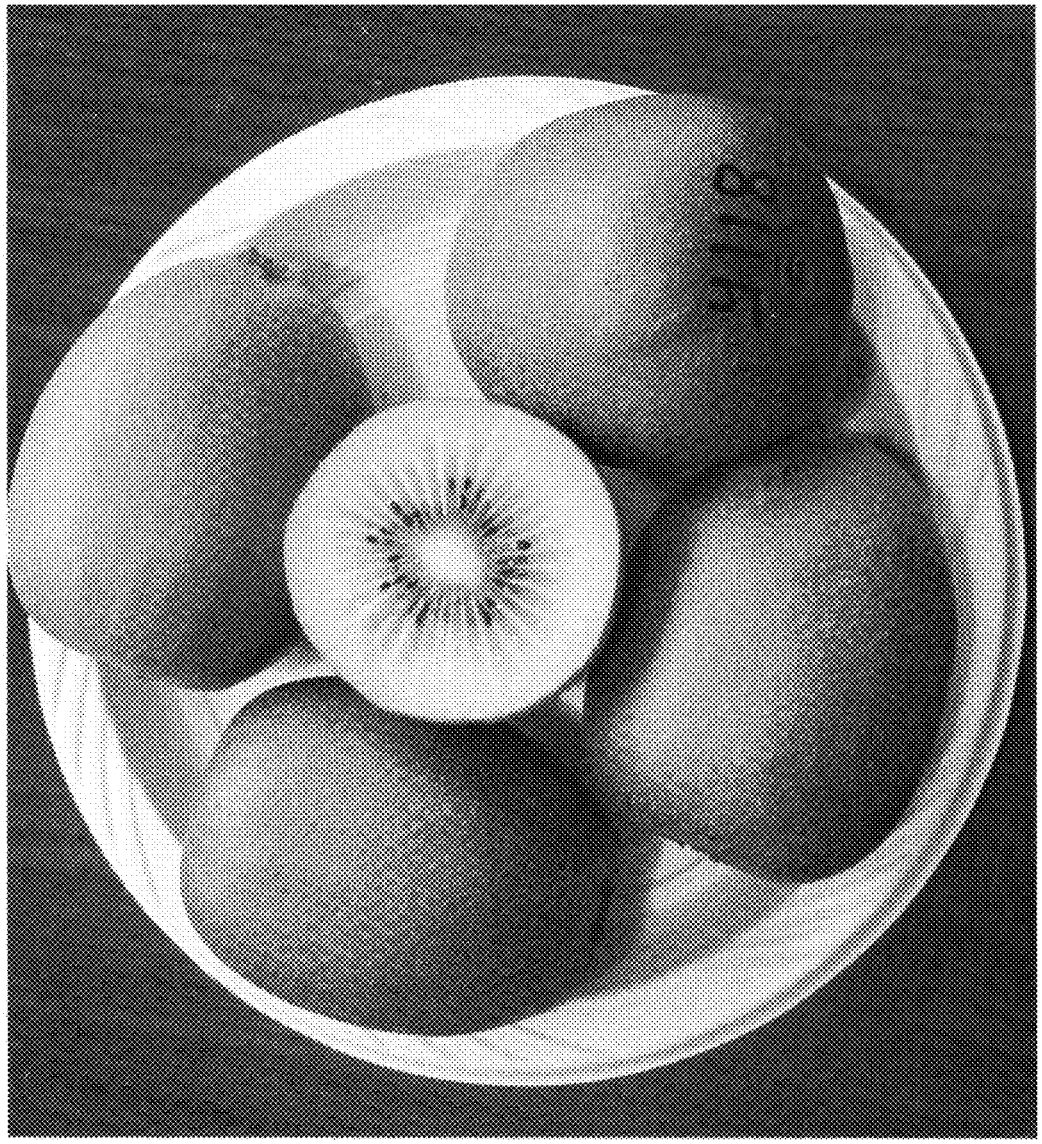

The accompanying photograph in FIG. 1 illustrates in full color typical foliage and flowers on plants of 'Y118.' FIG. 2 illustrates in full color typical flowers of 'Y118.' FIG. 3 shows examples of typical fruit harvested from 'Y118.' All photographs were taken of an approximately 9 year old plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Y118' plants grown under outdoor commercial trial conditions in Rangiriri New Zealand. The growing temperature ranged from 10° C. to 25° C. with no precipitation. Measurements and numerical values represent averages of typical plant types Botanical classification: *Actinidia chinensis* Y118.

PROPAGATION

'Y118' can be successfully grafted onto rootstocks of *Actnidia chinensis* or *Actinidia deliciosa*.

PLANT

*Sex Expression.*—Female
*Ploidy.*—Diploid
*Vigor.*—Moderately high vigor. On a scale of 1 to 10 with 10 being the highest 'Y118' is a comparative 8 among commercial *Actinidia* varieties,.
*Young shoot color.*—Near RHS Green 137C.
*Young shoot texture.*—Smooth, non-pubescent and no visible lenticels.
*Stem diameter.*—Average 1 cm.
*Stem texture.*—Rough.
*Trunk diameter.*—Average 3.5 cm on a 9 year old plant.
*Stem Lenticels.*—Stem lenticels either not present or barely visible to the eye.
*Age of the Plant Described.*—Approximately 9 years.

FOLIAGE

Leaf:
*Average Length.*—Range between 17.3–20.0 cm.
*Average Width.*—Range between 13.8–16.5 cm.
*Shape of blade.*—Very broadly ovate.
*Apex.*—Rounded.
*Base.*—Cordate, overlapping.
*Attachment.*—Petioled.
*Margin.*—Ciliate.
*Texture of top surface.*—Very slightly puckered non-pubescent.
*Texture of under side.*—Moderately glossy, non-pubescent.
*Color.*—Mature foliage upper side: Near RHS Green 138A. Mature foliage under side: Near RHS Green 141C.
*Petiole.*—Length: Range between 13.8–16.5 cm. Pubescence: None. Color: Near RHS Green 143C with flush of Greyed-Purple N186C on upperside of petiole.

FLOWER

*Flowers per Inflorescence.*—Most often 3.
*Bud color.*—Near RHS Yellow-Green 144C.
*Bud Break. Early September.*
*First Flower.*—Early October.
*Diameter.*—Average 4.7 cm.
*Petal Quantity.*—6 or 7 per flower.
*Petals Overlapping.*—Yes.
*Color.*—Near RHS White 155A.
*Filament color.*—White.
*Anther Color.*—Yellow/brown.
*Attitude of Styles.*—Semi-erect.
*Style Color.*—Near RHS Yellow-Green 154D.
*Style Quantity.*—Average 17.
*Hair on Ovary.*—Dense.
*Color of Ovary.*—White.
*Number of Sepals.*—6 to 7.
*Color of Sepals.*—Near RHS Green 141C.
*Sepal Width.*—Approximately 1.1 cm.
*Sepal Length.*—Approximately .8 cm.
*Sepal Texture.*—Smooth.

Peduncle:
*Length.*—Average 6.2 cm.
*Color.*—Near RHS Yellow-Green 144B.
*Texture.*—Smooth.

FRUIT

*Color outer pericarp.*—Near RHS Yellow 3D.
*Color inner pericarp Near RHS Yellow* 2C.
*Core color.*—Near RHS Yellow-White 158D.
*Brix at consumption.*—16.8-18.3
*Brix at Harvest.*—8.00%.
*Average weight.*—110 grams.
*Minimum weight.*—95 grams.
*Maximum weight.*—110 grams.
*Length.*—Avg. 70 mm.
*Width.*—Avg. 50 mm.
*Core diameter(maximum).*—19.0 mm.
*Core diameter(minimum).*—5.0 mm.
*Locule number.*—30.
*Fruit Peduncle length.*—33 mm.
*Fruit Peduncle width.*—2.9 mm.
*General Shape.*—Oblong.
*Median cross section.*—Oval.
*Stylar end shape.*—Slightly blunt protruding.
*Shoulder shape.*—Squared.
*Calyx ring.*—Present.
*Calyx ring expression.*—Moderate.
*Skin color at harvest.*—Near RHS Yellow-Green 148 A
*Lenticels on fruit.*—Not present.
*Hair on fruit skin.*—Downy.
*Hair adherence to skin.*—Weak.
*Hair adherence to skin.*—Weak.
*Skin adherence to flesh at maturity.*—Moderate.
*Fruit core shape.*—Elliptic.
*Core-woody spike.*—Medium.
*Mature seed color.*—Black.
*Dried seed.*—Brown.
*Harvest time.*—Late March.
*Overall cropping quantity.*—Heavy.

OTHER CHARACTERISTICS

Storage life: Storage life is a minimum of 3 months at 2° C.
Disease/pest resistance: Neither resistance nor susceptibility to pathogens and pests common to *Actinidia chinensis* have been observed.
Temperature tolerance: Tolerates low temperatures to approximately −8° C. without negative effects, tolerates high temperatures to approximately 35° C. without negative effects.

What is claimed is:

1. A new and distinct cultivar of *Actinidia chinensis* plant named 'Y118' as herein illustrated and described.

* * * * *